United States Patent [19] [11] 4,447,664
Murchison et al. [45] May 8, 1984

[54] INTEGRATED FISCHER-TROPSCH AND AROMATIC ALKYLATION PROCESS

[75] Inventors: Craig B. Murchison; Robert A. Stowe; Richard L. Weiss, all of Midland, Mich.

[73] Assignee: The Dow Chemical Company, Midland, Mich.

[21] Appl. No.: 422,317

[22] Filed: Sep. 23, 1982

[51] Int. Cl.$^3$ .............................................. C07C 2/68
[52] U.S. Cl. ................................. 585/323; 585/467; 518/714
[58] Field of Search ................. 585/323, 467; 518/714

[56] References Cited

U.S. PATENT DOCUMENTS

| | | | |
|---|---|---|---|
| 3,674,885 | 7/1972 | Griesinger et al. | 585/323 |
| 3,751,506 | 8/1973 | Burress | 260/671 R |
| 3,962,364 | 6/1976 | Young | 260/671 C |
| 4,016,218 | 4/1977 | Haag et al. | 260/671 R |
| 4,104,319 | 8/1978 | Kaeding | 260/671 C |
| 4,107,224 | 8/1978 | Dwyer | 260/671 R |
| 4,151,190 | 4/1979 | Murchison et al. | 260/449 R |
| 4,199,522 | 4/1980 | Murchison et al. | 518/714 |
| 4,367,359 | 1/1983 | Kaeding | 585/467 |
| 4,380,589 | 4/1983 | Murchison et al. | 518/714 |

OTHER PUBLICATIONS

Mobil/Badger, *Chemical Engineering*, Dec. 5, 1977, pp. 120–121, Linde SK-500, Product Report.

Catalysis, vol. I, Anderson et al., Springer-Verlag, New York, 1981, pp. 169–175.

Ethylene, *Hydrocarbon Processing*, Nov. 1981, pp. 157 & 158.

*Primary Examiner*—Curtis R. Davis
*Attorney, Agent, or Firm*—Charles J. Enright

[57] ABSTRACT

The disclosure describes a process for alkylating aromatics comprising the steps of:

(1) contacting a mixture of hydrogen and carbon monoxide with a Fischer-Tropsch catalyst at conditions effective to form a first gas mixture containing an alkylating agent selected from ethylene or mixtures of ethylene and propylene;

(2) removing from the first gas mixture components capable of alkylating aromatics and having boiling points higher than the selected alkylating agent to form a second gas mixture which contains less than about 10 mole percent of the selected alkylating agent and more than about 5 mole percent each of carbon monoxide and hydrogen;

(3) combining the second gas mixture with sufficient alkylatable aromatic hydrocarbon to form a third mixture containing at least about a 1 to 1 aromatic to alkylating agent mole ratio; and (4) contacting the third mixture with a heterogeneous alkylation catalyst at conditions effective to alkylate the aromatic hydrocarbon.

20 Claims, No Drawings

INTEGRATED FISCHER-TROPSCH AND AROMATIC ALKYLATION PROCESS

FIELD OF THE INVENTION

The invention relates to a process for making cumene, ethylbenzene and other alkyl aromatics by coupling a Fischer-Tropsch process for making propylene and/or ethylene and a process for alkylating aromatics.

BACKGROUND OF THE INVENTION

Styrene, an important commodity chemical used to make plastics, is generally made by the dehydrogenation of ethylbenzene. The intermediate ethylbenzene may be derived as a by-product of catalytic reforming or by alkylating benzene with ethylene.

Cumene or isopropylbenzene is also a commodity chemical used for making phenol and α-methylstyrene. It may be derived from distillation of coal tar or petroleum or by the alkylation of benzene with propylene.

U.S. Pat. No. 4,107,224; which is hereby incorporated by reference, discloses a process for ethylating benzene by contacting benzene and a dilute ethylene stream with a ZSM-5 type zeolite. The molar concentration of ethylene in the dilute ethylene stream is generally more than 15 percent. The molar concentration of carbon monoxide is generally less than 5 percent. The hydrogen to carbon monoxide ratio is also high.

The Fischer-Tropsch process as practiced commercially today is described in Chapter 4 of *Catalysis, Science and Technology*, Vol. 1, by M. E. Dry which is incorporated herein by reference. In general, a carbonaceous material is first gasified to hydrogen and carbon monoxide. This raw gas is then purified and passed through a catalytic Fischer-Tropsch reactor. Water, carbon dioxide and hydrocarbons and oxygenates which are liquid at ambient temperatures are separated from the gases. The gaseous products including unconverted hydrogen and carbon monoxide and the hydrocarbons having 4 or less carbons, are then cryogenically separated into the various components. Purified ethylene may then be reacted with aromatic hydrocarbons in the presence of heterogeneous alkylation catalysts such as described in U.S. Pat. No. 3,751,506; which is herein incorporated by reference.

Due to the low boiling points of hydrogen and carbon monoxide, the Fischer-Tropsch process is generally run at a conversion of at least 60 percent and preferably at least 80 percent to reduce the amount of hydrogen and carbon monoxide that must be separated from the light hydrocarbons. A disadvantage of operating the Fischer-Tropsch process at high conversions is that the selectivity to ethylene is lower.

OBJECTS OF THE INVENTION

It is an object of this invention to recover and use small amounts of propylene and/or ethylene from a Fischer-Tropsch product stream without the expense of purifying propylene and/or ethylene. It is a preferred object of this invention that propylene and/or ethylene produced in a Fischer-Tropsch reaction be employed in an end-use without requiring that it be cryogenically separated from methane, carbon monoxide and hydrogen present in the product stream. It is a preferred object of this invention to use the propylene and/or ethylene produced in a Fischer-Tropsch reaction to alkylate aromatics without separating the propylene and/or ethylene from lower boiling components in the Fischer-Tropsch product mix. It is a further preferred object of this invention to operate the Fischer-Tropsch reaction at low conversion in order to maximize the selectivity to propylene and/or ethylene which is then used to alkylate aromatics with lower purification costs.

SUMMARY OF THE INVENTION

This and other objects of the invention are achieved by a process for alkylating an aromatic hydrocarbon comprising the steps of:
(1) contacting a mixture of hydrogen and carbon monoxide with a Fischer-Tropsch catalyst at conditions effective to form a first gas mixture containing an alkylating agent selected from ethylene or mixtures of ethylene and propylene;
(2) removing from the first gas mixture components capable of alkylating aromatics and having boiling points higher than the selected alkylating agent, to form a second gas mixture which contains less than about 10 mole percent of the selected alkylating agent and more than about 5 mole percent each of carbon monoxide and hydrogen;
(3) combining the second gas mixture with sufficient alkylatable aromatic hydrocarbon to form a third mixture containing at least about a 1 to 1 aromatic to alkylating agent mole ratio; and
(4) contacting the third mixture with a heterogeneous alkylation catalyst at conditions effective to alkylate the aromatic hydrocarbon.

An advantage of this invention is that the Fischer-Tropsch reaction may be adjusted to increase the selectivity to ethylene without regard for cryogenically separating ethylene from unconverted feed. An additional advantage is that the process combines an advantageous source of propylene and/or ethylene and a major use for propylene and/or ethylene without requiring intermediate separation of pure components.

DETAILED DESCRIPTION OF THE INVENTION

The hydrogen and carbon monoxide required for this process may be obtained by methods known in the art. Examples are gasification of hydrocarbonaceous material such as coal, high specific gravity oils or natural gas; as a by-product of partial combustion cracking; or through the water-gas shift reaction. The two components may also be generated separately and combined for the subject reaction.

The molar ratio of hydrogen to carbon monoxide ranges generally from about 0.25 to about 4.0 and preferably from about 0.5 to about 1.5. Catalysts and operating conditions for the Fischer-Tropsch process are described, for example, in U.S. Pat. Nos. 4,151,190; 4,199,522 or any others which have a high selectivity to ethylene. A preferred catalyst is described in a copending patent application Ser. No. 368,536; filed April 15, 1982. All of these references are incorporated herein by reference.

A preferred catalyst composition comprises in combination, discrete particles of molybdenum in free or combined form and a promoter comprising an alkali metal or alkaline earth metal in free or combined form. These two components are bound with a binder formed by pyrolyzing an organic material in contact with the molybdenum and promoter. A feature of the preferred catalyst is the large crystallites of molybdenum in the catalyst. This is the result of agglomerating discrete particles rather than dispersing molecular molybdenum as with solution impregnation of supports.

The Fischer-Tropsch process conditions can vary over a broad range. Generally they will fall within the bounds known to the art. The pressure can vary from atmospheric to about 1500 psig and preferably from about 150 psig to about 500 psig. The process temperature ranges from about 150° C. to about 500° C. and preferably from about 300° C. to about 420° C.

The selectivity to ethylene may be improved by reducing the carbon monoxide conversion in the Fischer-Tropsch process reaction. With the potassium promoted molybdenum-titanium catalyst, selectivity to ethylene at 20 percent conversion may be as high as 20 carbon mole percent whereas at conversions of greater than 60 percent selectivity to ethylene may be less than 10 carbon mole percent. Conversion may be lowered, for example, by increasing the space velocity of reactants. Thus, for a given catalyst at a high space velocity and low conversion, the pounds per hour of ethylene per pound of catalyst may be higher than at lower space velocities and concurrent higher conversion. Advantageously, the conversion in the Fischer-Tropsch reaction is less than 50 percent in order to improve the selectivity to ethylene. More advantageously, the conversion is less than 30 percent and most advantageously the conversion is from about 20 to about 25 percent. Advantageously conversion is lowered by increasing the space velocity of reactants.

A more dilute ethylene feed to the alkylation step is advantageous because the more dilute the selected alkylating agent is, the more difficult it is to purify and use, and thus the more benefit is derived from the inventive process.

In either the high or low conversion cases, the concentration of the selected alkylating agent in the first hydrocarbon mixture is very low. Generally, it is less than 2 mole percent. The Fischer-Tropsch process effluent which makes up the first hydrocarbon mixture also contains substantial hydrogen and carbon monoxide when the process is operated at low conversions. The Fischer-Tropsch process effluent may contain at least 5 mole percent each of hydrogen and carbon monoxide. Lower conversions directly result in higher concentrations of carbon monoxide and hydrogen. Generally, the effluent contains more than 10 mole percent each and advantageously contains more than 15 mole percent each of hydrogen and carbon monoxide.

Prior to the alkylation of the aromatic material, alkylating agents which are capable of alkylating aromatic materials other than the selected alkylation agent must be substantially removed from the first hydrocarbon mixture. By substantially removed it is meant that the components of the first hydrocarbon mixture which are capable of alkylating aromatic hydrocarbons are removed to a level which is commercially practiced. One hundred percent removal is not practical. A concentration of less than about 10 mole percent of non-selected alkylating agent as a percent of all alkylating agent is preferred. Less than about 5 mole percent is more preferred. This may be done by condensing all alkylating agents which boil at a temperature higher than the boiling point of the selected alkylating agent. This leaves a second gas mixture which contains a mixture of ethane, ethylene, methane, carbon monoxide and hydrogen which may also contain propane and propylene and which can be used directly to alkylate the aromatic material.

If the selected alkylating agent is ethylene, one removes propylene and higher boiling alkylating agents. If the selected alkylating agent is an ethylene/propylene mixture, one removes isobutane, butylenes and higher boiling alkylating agents. Propane and ethane are not considered alkylating agents in this process and need not be removed. Ethylene is the preferred alkylating agent.

An alternative method of removing alkylating agents with higher boiling points is by removing only part of the hydrocarbons which boil higher than the selected alkylating agent and reacting the balance of the alkylating agents in a reaction in which the selected alkylating agent selectively does not react. An example is the process disclosed in U.S. Pat. No. 4,227,992, which is incorporated herein by reference. This patent discloses a process wherein propylene is selectively removed from a propylene/ethylene mixture by passing it over a zeolite such as ZSM-5 at critical reaction temperatures and pressures. Species which would alkylate the aromatics under the ethylation conditions include propylene, butylenes and oxygenated materials formed in the Fischer-Tropsch process. Other methods of removing higher boiling alkylating agents known to those skilled in the art are considered to be within the scope of this invention.

Removal of alkylating agents having boiling points higher than the selected alkylating agent forms a second gas mixture which contains less than 10 mole percent of the selected alkylating agent and more than 5 mole percent each of carbon monoxide and hydrogen. Advantageously, the second gas mixture contains less than 5 percent of the selected alkylating agent and most advantageously contains less than 1 percent. The second gas mixture advantageously contains more than 10 mole percent each of carbon monoxide and hydrogen and more advantageously contains more than 15 mole percent each.

The second gas mixture is then combined with sufficient aromatic hydrocarbon to yield a third mixture containing at least a 1 to 1 aromatic to alkylating agent molar ratio. The molar ratio of the aromatic compound to the alkylating agent is set high in order to obtain higher conversion of the selected alkylating agent and to minimize oligomerization of the alkylating agent and other side reactions. Preferably the mole ratio of aromatic to alkylating agent is at least 10 to 1.

The aromatic hydrocarbon may be mono- or polynuclear and may have alkyl side chains or inertly-substituted alkyl side chains. Benzene, toluene and naphthalene are preferred aromatic hydrocarbons and benzene is most preferred.

This third mixture is then contacted with a heterogeneous alkylation catalyst at conditions effective to alkylate the aromatic. Heterogeneous alkylation catalysts effective for this reaction are known to those skilled in the art. Examples are the zeolites such as X, Y, SK-500, and ZSM-5. Other heterogeneous alkylation catalysts useful in this process include high silica analogues of X, Y, SK-500; ZSM-5 which can be substituted with boron, iron, chromium or other elements; ZSM-11 or their equivalents; various silicalites; NU-1, FU-1 and others.

The alkylation catalysts and process conditions are disclosed, for example, in U.S. Pat No. 4,107,224, which is incorporated herein by reference. The specific reaction conditions of the alkylation will vary from one catalyst to another, but will generally be in the following ranges. Temperatures for the alkylation reaction of from about 250° C. to about 600° C. are operable. The preferred temperature range is from about 350° C. to about 450° C. Operable pressures include atmospheric to about 1500 psig. A preferred range is from about 1 psig to about 500 psig.

The following examples are considered illustrative of the process of the invention. Elements of the Fischer-Tropsch catalysts are given as weight percent of component added to the catalyst precursor not including volatile fluid added for processing. The percentage of each component given in the following tables is generally based on the weight of the dry powder prior to water addition and subsequent treatments of the catalyst such as calcination and reduction which tend to alter the final composition.

Subscripts, e.g., the 1 in $C_1$, etc., in all examples indicate the number of carbon atoms. Hydrocarbon analyses are reported in carbon mole percent in the Fischer-Tropsch reaction step examples. "Carbon mole percent" is defined as 100 times the moles of carbon present in a hydrocarbon fraction divided by the total moles of carbon in the product hydrocarbon. For example, if one mole of ethylene is found in the $C_2$ fraction, this is counted as 2 moles of carbon. The term "product hydrocarbon" excludes any carbon dioxide produced.

In the Fischer-Tropsch examples, an apparatus is utilized which includes in sequential order three high pressure gas bottles, a manifold, and reactors equipped on the downstream side with a fine metering valve and a rotameter, a sampling manifold and a gas chromatograph. Two bottles contain mixtures of hydrogen, carbon monoxide and nitrogen. The mixtures permit varying of the $H_2/CO$ ratio from about 0.5 to about 3.0. The third bottle contains hydrogen. Each bottle is independently connected to the manifold. The manifold is constructed such that any of the three bottles may be used to feed the reactor. Through the sampling manifold the product of each reactor may be piped to the gas chromatograph for analysis.

The catalysts are loaded into ½ inch internal diameter reactors and are reduced in hydrogen before being used. The reactors are then brought to operating temperature in the presence of hydrogen. Next, feed from the high pressure gas bottle containing hydrogen and carbon monoxide is allowed to flow through the manifold to the reactor. Pressure, flow and temperature are adjusted to operating values.

The general procedure for making the catalysts for the Fischer-Tropsch reaction examples is by combination of the dry powders of the ingredients and moistening with water to make a smooth but moderately stiff paste. This paste is then extruded through an extruder such as a common laboratory syringe. The extruded paste is then dried and pyrolyzed at 100° C.–700° C. and then reduced at 400° C.–700° C. The pyrolysis preferably is conducted in an inert atmosphere. The reduction is preferably conducted using hydrogen as the reducing agent.

EXAMPLES 1A and 1B

Coal tar (2.5 g) (Allied Chemical S.P. 107-113G), hydroxypropyl methylcellulose (2.5 g) (The Dow Chemical Company, Methocel HG ®), potassium carbonate (1.0 g), titanium dioxide (22.0 g) (DuPont LW Grade), molybdenum trioxide (22.0 g) (Climax Molybdenum, undensified), all as dry powders are mixed and then blended with 39 ml of water to form a paste which is extruded into about 1/16 inch pellets using a 20 cc plastic syringe. The pellets are then air dried to yield the following composition, based on components added:
- 44% molybdenum oxide ($MoO_3$);
- 44% titanium dioxide ($TiO_2$);
- 2% potassium carbonate ($K_2CO_3$);
- 5% coal tar; and
- 5% cellulose ether.

The dried pellets were then calcined at up to 700° C. in hydrogen for 3 hours. The rate of temperature rise in the oven is 2° C./min from 340° C. up to 700° C.

The calcined catalyst (15 cc, 10.85 g) is loaded into the reactor and reduced with flowing hydrogen at 560° C. for 64 hours.

Examples 1A and 1B differ in the space velocity and accordingly in conversion, carbon selectivity to ethylene and the pounds per hour of ethylene per cubic foot of catalyst. The reaction conditions and results are set out in Table I.

TABLE I

|  | 1A | 1B |
| --- | --- | --- |
| Temperature °C. | 407 | 420 |
| Pressure psig | 500 | 500 |
| GHSV ($hr^{-1}$) | 1724 | 236 |
| CO Conversion % | 25 | 67 |
| Feed |  |  |
| $H_2$ | 39.8 | 39.8 |
| CO | 55.0 | 55.0 |
| $N_2$ | 5.2 | 5.2 |
| Products (mole %) |  |  |
| $H_2$ | 34.13 | 19.92 |
| CO | 47.01 | 28.77 |
| $N_2$ | 6.00 | 8.24 |
| $CH_4$ | 2.41 | 9.10 |
| $C_2H_6$ | 0.38 | 1.90 |
| $C_2H_4$ | 0.79 | 1.01 |
| $C_3H_8$ | 0.08 | 0.71 |
| $C_3H_6$ | 0.27 | 0.83 |
| $C_4+$ | 0.31 | 1.65 |
| $CO_2$ | 8.62 | 27.98 |
|  | 100.0 | 100.0 |

In Example 1A, 0.92 pound of ethylene per cubic foot of catalyst per hour is produced. In Example 1B, 0.128 pound are produced. After removal of $C_3+$ and carbon dioxide, the two product gases contain 0.87 and 1.47 mole percent ethylene, respectively.

EXAMPLES 2A and 2B

In this Example a more conventional Fischer-Trospch catalyst is used. The catalyst is made by sintering extruded powders of the components at 1000° C. The catalyst composition is 27.0 percent $Fe_2O_3$; 70 percent $TiO_2$; 1.5 percent ZnO; and 1.5 percent $K_2CO_3$. Example 2A was taken after 118 hours on stream. Example 2B was taken after 335 hours on stream. In this case, conversion is changed primarily by aging the catalyst. The reaction conditions and results are set out in Table II.

TABLE II

|  | 2A | 2B |
| --- | --- | --- |
| Temperature °C. | 318 | 330 |
| Pressure psig | 150 | 200 |
| GHSV ($hr^{-1}$) | 776 | 992 |
| CO Conversion % | 25 | 98 |
| Feed (mole %) |  |  |
| $H_2$ | 40.8 | 40.8 |
| CO | 54.6 | 54.6 |
| $N_2$ | 4.5 | 4.5 |
| Products (mole %) |  |  |
| $H_2$ | 38.63 | 11.55 |

TABLE II-continued

|       | 2A    | 2B    |
|-------|-------|-------|
| CO    | 45.38 | 2.32  |
| $N_2$ | 4.91  | 9.73  |
| $CH_4$ | 1.09 | 8.20  |
| $C_2H_4$ | 0.51 | 0.61 |
| $C_2H_6$ | 0.18 | 2.91 |
| $C_3H_8$ | 0.55 | 3.54 |
| $C_3H_6$ | 0.05 | 1.33 |
| $C_{4+}$ | 0.70 | 6.30 |
| $CO_2$ | 8.00 | 54.22 |
| after removal of $CO_2$ and $C_{3+}$ | | |
| $H_2$ | 42.59 | 33.38 |
| CO    | 50.03 | 6.70  |
| $N_2$ | 5.41  | 28.12 |
| $CH_4$ | 1.20 | 23.70 |
| $C_2H_4$ | 0.56 | 1.76 |
| $C_2H_6$ | 0.20 | 6.33 |

EXAMPLE 3

The Alkylation Step

The feed gas to the alkylation step is a mixture comprising 50.9 mole percent hydrogen, 26.7 mole percent carbon monoxide, 12.5 mole percent methane, 3.9 mole percent ethylene, 2.7 mole percent ethane and 3.2 mole percent nitrogen. This mixture is chosen to represent a possible Fischer-Tropsch product stream after removal of water, carbon dioxide, propylene and higher boiling point hydrocarbons. Benzene is added to this feed gas to yield a benzene to ethylene mole ratio of 14.4 to 1.0. This resulting mixture is passed through a tubular reactor containing ZSM-5 zeolite with a silica to alumina ratio of about 80. The pressure is about 50 psig. The temperature is about 400° C. and the feed rate is about 152 ghsv based on ethylene.

About 75 percent of the ethylene is converted. Of the ethylene converted, 82 percent forms ethylbenzene and 8 percent forms diethylbenzene.

EXAMPLE 4

Another synthetic Fischer-Tropsch product gas is used to alkylate benzene. The gas has the following composition in mole percent.

|          |       |
|----------|-------|
| $H_2$    | 58.40 |
| $C_2H_4$ | 3.35  |
| $C_2H_6$ | 2.26  |
| $N_2$    | 3.03  |
| $CH_4$   | 10.53 |
| CO       | 22.43 |

Benzene is added to this gas to yield a benzene to ethylene mole ratio of 17.5 to 1. This resulting mixture is passed through a tubular reactor containing HZSM-5 diluted 50/50 with alumina under the following conditions. The pressure is 50 psig and the temperature is 400° C. The gas product from the alkylation process contains in mole percent:

|          |       |
|----------|-------|
| $H_2$    | 57.9  |
| CO       | 24.94 |
| $N_2$    | 3.06  |
| $CH_4$   | 11.63 |
| $C_2H_4$ | 0.075 |
| $C_2H_6$ | 2.37  |
| $C_3H_6$ | 0.032 |

The liquid product stream contains in weight percent:

|               |       |
|---------------|-------|
| benzene       | 91.14 |
| toluene       | 0.15  |
| ethylenebenzene | 8.28 |
| diethylbenzene | 0.24 |
| xylene        | 0.19  |

This represents 97.8 percent removal of ethylene and 96.2 percent selectivity to ethylbenzene.

Although the invention has been described in considerable detail, it must be understood that such detail is for the purpose of illustration only and that many variations and modifications can be made by one skilled in the art without departing from the spirit and scope of the invention.

What is claimed is:

1. A process for alkylating an aromatic hydrocarbon comprising:
   (1) contacting a mixture of hydrogen and carbon monoxide with a Fischer-Tropsch catalyst at conditions effective to form a first gas mixture containing an alkylating agent selected from ethylene or mixtures of ethylene and propylene;
   (2) removing from the first gas mixture components capable of alkylating aromatics and having boiling points higher than the selected alkylating agent to form a second gas mixture which contains less than about 10 mole percent of the selected alkylating agent and more than about 5 mole percent each of carbon monoxide and hydrogen;
   (3) combining the second gas mixture with sufficient alkylatable aromatic hydrocarbon to form a third mixture containing at least about a 1 to 1 aromatic to alkylating agent mole ratio; and
   (4) contacting the third mixture with a heterogeneous alkylation catalyst at conditions effective to alkylate the aromatic hydrocarbon.

2. The process of claim 1 wherein less than 50 percent of the carbon monoxide is converted to hydrocarbons in step (1).

3. The process of claim 2 wherein less than 25 percent of the carbon monoxide is converted to hydrocarbons in step (1).

4. The process of claim 3 wherein the catalyst used in step (1) comprises:
   (a) discrete particles of molybdenum in free or combined form;
   (b) a promoter comprising an alkali metal or alkaline earth metal in free or combined form; and
   (c) a carbonaceous binder formed by pyrolyzing an organic material in contact with the molybdenum and promoter.

5. The process of claim 1 wherein the catalyst used in step (1) contains molybdenum and an alkali or alkaline earth metal.

6. The process of claim 1 wherein the second gas mixture contains less than 5 mole percent of the selected alkylation agent.

7. The process of claim 6 wherein the second gas mixture contains less than 1 mole percent of the selected alkylation agent.

8. The process of claim 1 wherein the second gas mixture contains more than 10 mole percent each of carbon monoxide and hydrogen.

9. The process of claim 1 wherein the second gas mixture contains more than 15 mole percent each of carbon monoxide and hydrogen.

10. The process of claim 1 wherein the components removed in step (2) are removed cryogenically.

11. The process of claim 1 wherein the components removed in step (2) are removed by reacting at least a portion of the first gas mixture at conditions to selectively react components having boiling points higher than ethane and which are capable of alkylating aromatics.

12. The process of claim 1 wherein the third mixture contains at least a 10 to 1 molar ratio of aromatic to the selected alkylating agent.

13. The process of claim 1 wherein the alkylatable aromatic hydrocarbon is benzene.

14. The process of claim 1 wherein the heterogeneous alkylation catalyst is a zeolite.

15. The process of claim 14 wherein the heterogeneous alkylation catalyst is a ZSM-5 zeolite.

16. The process of claim 1 wherein the selected alkylating agent is a mixture of propylene and ethylene.

17. The process of claim 1 wherein the selected alkylating agent is ethylene.

18. The process of claim 1 wherein step (1) is adjusted to increase the selectivity to the alkylating agent.

19. The process of claim 18 wherein step (1) is adjusted by lowering the conversion of carbon monoxide.

20. The process of claim 19 wherein the conversion is lowered by increasing the hydrogen and carbon monoxide space velocity.

* * * * *